US006645726B1

(12) United States Patent
Howard et al.

(10) Patent No.: US 6,645,726 B1
(45) Date of Patent: Nov. 11, 2003

(54) CANINE GROWTH HORMONE SECRETAGOGUE RECEPTOR

(75) Inventors: Andrew D. Howard, Park Ridge, NJ (US); Oksana C. Palyha, Fords, NJ (US); Carina P. Tan, Metuchen, NJ (US); Roy G. Smith, Houston, TX (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/762,661

(22) PCT Filed: Aug. 6, 1999

(86) PCT No.: PCT/US99/17915

§ 371 (c)(1),
(2), (4) Date: May 30, 2001

(87) PCT Pub. No.: WO00/09538

PCT Pub. Date: Feb. 24, 2000

Related U.S. Application Data

(60) Provisional application No. 60/095,960, filed on Aug. 10, 1998.

(51) Int. Cl.$^7$ ...................... G01N 33/567; G01N 33/53; C12P 21/06; C12N 15/74; C12N 5/02

(52) U.S. Cl. ...................... 435/7.21; 435/7.1; 435/69.1; 435/320.1; 435/325; 530/300; 530/350; 530/399; 536/23.5; 536/24.3

(58) Field of Search .................... 530/350, 300, 530/399; 435/69.1, 7.21, 320.1, 7.1, 325; 536/23.5, 24.3

(56) References Cited

U.S. PATENT DOCUMENTS

| 3,239,345 | A | 3/1966 | Hodge et al. |
| 4,036,979 | A | 7/1977 | Asato |
| 4,410,513 | A | 10/1983 | Momany |
| 4,411,890 | A | 10/1983 | Momany |
| 5,057,417 | A | 10/1991 | Hammonds et al. |
| 5,206,235 | A | 4/1993 | Fisher et al. |
| 5,245,011 | A | 9/1993 | Tiberi et al. |
| 5,283,241 | A | 2/1994 | Bochis et al. |
| 5,284,841 | A | 2/1994 | Chu et al. |
| 5,310,737 | A | 5/1994 | Fisher et al. |
| 5,317,017 | A | 5/1994 | Ok et al. |
| 5,374,721 | A | 12/1994 | Schoen et al. |
| 5,422,265 | A | 6/1995 | Civelli et al. |
| 5,430,144 | A | 7/1995 | Schoen et al. |
| 5,434,261 | A | 7/1995 | Schoen et al. |
| 5,438,136 | A | 8/1995 | Devita et al. |
| 5,492,916 | A | 2/1996 | Morriello et al. |
| 5,492,920 | A | 2/1996 | Chen et al. |
| 5,494,919 | A | 2/1996 | Morriello et al. |
| 5,583,010 | A | 12/1996 | Baumbach et al. |
| 5,591,641 | A | 1/1997 | Thorner et al. |
| 6,242,199 | B1 * | 6/2001 | Pui et al. ............ 435/7.2 |
| 6,531,314 | B1 | 3/2003 | Arena et al. |

FOREIGN PATENT DOCUMENTS

| EP | 0 144 230 | 3/1984 |
| EP | 0 513 974 | 12/1992 |
| WO | WO 89/07110 | 8/1989 |
| WO | WO 89/07111 | 8/1989 |
| WO | WO 93/04081 | 3/1993 |
| WO | WO 94/07486 | 4/1994 |
| WO | WO 94/07915 | 4/1994 |
| WO | WO 94/08583 | 4/1994 |
| WO | WO 94/11012 | 5/1994 |
| WO | WO 94/13696 | 6/1994 |
| WO | WO 94/19367 | 9/1994 |
| WO | WO 95/03289 | 2/1995 |
| WO | WO 95/03290 | 2/1995 |
| WO | WO95/09633 | 4/1995 |
| WO | WO 95/11029 | 4/1995 |
| WO | WO 95/12598 | 5/1995 |
| WO | WO 95/13069 | 5/1995 |
| WO | WO 95/14666 | 6/1995 |
| WO | WO 95/16675 | 6/1995 |
| WO | WO 95/16692 | 6/1995 |
| WO | WO 95/17422 | 6/1995 |
| WO | WO 95/17423 | 6/1995 |
| WO | WO 95/34311 | 12/1995 |
| WO | WO 96 02530 | 2/1996 |
| WO | WO 97/21730 | 6/1997 |
| WO | WO 97/22004 | * 6/1997 |

OTHER PUBLICATIONS

Howard et al., Science, 1996, vol. 273(5277), pp. 974–977.*
Yokote, Ryoji et al. "Molecular Cloning and Gene Expression of Growth Hormone–Releasing Peptide Receptor in Rat Tissues". Peptides, vol. 19, No. 1, 1998, pp. 15–20.
Muruais, J. et al. "Influence of endogenous cholinergic tone and α–adrenergic pathways on growth hormone responses to His–D–Trp–Ala–D–Phe–Lys–NH2 in the dog". Journal of Endocrinology, vol. 138, No. 2, 1993, pp. 211–218.
Nelson, Allen H., et al. "Intranasal Activity of the Growth Hormone Releasing Peptide His–D–Trp–Ala–Trp–D–Phe–Lys–NH2 in Conscious Dogs". Life Sciences, vol. 48, No. 23, 1991, pp. 2283–2288.
Howard, A.D., et al. "A Receptor in Pituitary and Hypothalamus That Functions in Growth Hormone Release". Science, vol. 273, Aug. 1996, pp. 974–977.
Aloi, J., et al. "Neuroendocrine Responses to a Novel Growth Hormone Secretagogue, L–692, 429, in Healthy Older Subjects". Journal of Clinical Endocrinology and Metabolism, vol. 79, No. 4, 1994, pp. 943–949.

(List continued on next page.)

Primary Examiner—Lorraine Spector
Assistant Examiner—Janet L. Andres
(74) Attorney, Agent, or Firm—Patricia Chisholm; Jack L. Tribble

(57) ABSTRACT

A novel canine cDNA sequence that encodes the canine growth hormone secretagogue receptor (GHSR) protein is provided. Also provided is canine GHSR protein encoded by the novel cDNA sequence. Methods of expressing canine GHSR protein in recombinant systems are provided. Also provided are methods for identifying agonists and antagonists of the canine GHSR.

7 Claims, 4 Drawing Sheets

OTHER PUBLICATIONS

Bowers, C. "Editorial: On a Peptidomimetic Growth Hormone–Releasing Peptide". Journal of Clinical Endocrinology and Metabolism, vol. 79, No. 4, 1994, pp. 940–942.

Ok, D., et al. Structure–Activity Relationships of the Non–Peptidyl Growth Hormone Secretagouge L–692, 429, Bioorganic & Medicinal Chemistry Letters, vol. 4, No. 22, 1994, pp. 2709–2714.

Patchett, A., et al. "Design and biological activities of L–163, 191 (MK–0677): A potent, orally active growth hormone secretagogue". Proc. Natl. Acad. Sci. USA, vol. 92, Jul. 1995, pp. 7001–7005.

Schoen, W., et al. "Chapter 19, Section IV, Growth Hormone Secretagogues". Annual Reports in Medicinal Chemistry, vol. 28, 1993, pp. 177–183.

Smith, R., et al. "A Nonpeptidyl Growth Hormone Secretagogue". Science, vol. 260, Jun. 1993, pp. 1640–1643.

Sethumadhavan, K., et al. "Demonstration and Characterization of the Specific Binding of Growth Hormone–Releasing Peptide to Rat Anterior Pituitary and Hypothalamic Membranes". Biochem. Biophys. Res. Comm., vol. 178, 1991, pp. 31–37.

King, K., et al. "Control of Yeast Mating Signal Transduction by a Mammalian β2–Adrenergic Receptor and Gs a Subunit". Science, vol. 250, 1991, pp. 121–123.

Julius, et al. "Molecular Characterization of a Functional cDNA Encoding the Serotonin 1c Receptor". Science, vol. 241, 1998. pp. 558–564.

Cubitt, et al. "Understanding improving and using green flourescent proteins". Trends Biochem. Sci., vol. 20, 1995, pp. 448–455.

McKee, K., et al. "Molecular Analysis of Rat Pituitary and Hypothalamic Growth Hormone Secretagogue Receptors". Molecular Endocrinology, vol. 11, 1997, pp. 415–423.

Feighner, S., et al. "Structural Requirements for the Activation of the Human Growth Hormone Secretagogue Receptor by Peptide and Nonpeptide Secretagogues". Molecular Endocrinology, vol. 12, 1997, pp. 137–145.

Williams, "Textbook of Endocrinology". 1994, p. 790.

Grenade, et al. "Cloning of the porcine D1A dopamine receptor gene expressed in renal epithelial LLC–PK1 cells". American Journal of Physiology, vol. 268, No. 3, Part 2, 1995, pp. F423–F434.

Blake, et al. "Desensitization studies using perifused rat pituitary cells show that growth hormone–releasing hormone and His–D–Trp–Ala–Trp–D–Phe–Lys–NH2 stimulate growth hormone release through distinct receptor sites". Journal of Endocrinology, vol. 129, No. 1, 1991, pp. 11–19.

Pomes, A. et al., "Solubilization and Characterization of a Growth Hormone Secretagogue Receptor from Porcine Anterior Pituitary Membranes". Biochemical and Biophysical Research Communications, vol. 225, 1996, pp. 939–945.

Nargund, Ravi, P., et al. "Abstracts of Paper American Chemical Society". vol. 212, No. 1–2, 1996.

Pong, S–S., et al. "Indentification of a New G–Protein–Linked Receptor for Growth Hormone Secretagogues". Molecular Endocrinology, vol. 10, No. 1, 1996, pp. 57–61.

Hrenjuk, D., et al. Society for Neuroscience, vol. 22, No. 1–3, 1996, p. 1300.

Smith, R.G., et al. "Recent Progress in Hormone Research: Modulation of Pulsatile GH Release Through a Novel Receptor in Hypothalamas and Pituitary Gland". vol. 51, 1996, pp. 261–286.

* cited by examiner

ATGCGGAACGCGACGCCCGCGAGGCCCGGGGTCGGGGCTGGACCTGCTGCCGCTGTTCCCCGCG
CCGCTGCTGCGGGCGTGACGGCCACCTGCGGGTGCTGTTCGCCGTGGGCGTCGGGGCAACCTGCTG
ACGGTGCTGGTGCGGCGCTTCCGGCAGCTGCCGAGCTGTACCTGTACCTGTGCAGCCTGGCC
TGCTCCGACCTGCTCATCTTCTGTGCATCCGCTCGTGCCTGTGCCTGTGGCAGTACCGGCCTGG
ACCTTCGGGACCTGCTCTGCAAACTCTTCCAGTTCGTGAGCGAGGGCTGCACCTACGCCACGGTGCTC
ACCATCACGGCGCTGAGCGTCGAGCGGCTACTTCGGCCATCTGCTCCCGCTGCCGCCAAGGTGCTGGTG
ACCAAGGCCCGCGTCAAGCTGGACCTGCCCTGCCCTTCTGCAGCGCCCCGGGCCATC
TTCGTGCTGGTGGGGCGTGGAGCACGAGAACGGCACCCACCCCGGGACACCCGAGTGCCGGCCACC
GAGTTCGCCCTGCCGGCCTCGGGCTGCTCACGGCCCATGGTGTGGTGTCCAGCGTCTTCTTCCTGCCC
GTCTTCTGCCTCACGGTGCTCTACGGCCTCATCGGCAGGAAGCTGTGCGCAGAAGCTGTGCGGGCGACACN
GCGGGGGCGTCGCTCCGAGCAGAGCACCGGCAGAGCGGTGAAGATGCTCGCTGTCGTGTTT
GCTTTCATCTCTGCTGGCTGCCCTTCCACGTGGGGCGATATTTATTTCCAAGTCCTTGAGCCCGGC
TCCTTGGAGATTGCTCAGATCAGCCAATACTGCAACCTGGTATCCTTTGTCCTCTTCTACCTCAGTGCT
GCCATCAATCCCATTCTGTACAACATCATGTCCAAGAAGTACCGGGTGGCGGTGTTCAAGCTTCTGGA
TTGAACCCTCTCCCAGAGGAAGCTCTCCACTCTGAAGGATGAAAGTTCTCGGGCCTGGACAGAGTCT
AGTATTAATACATGA (SEQ.ID.NO.:1)

FIG.1

MRNATAREGPGSAGWDLLPLFPAPLLAGVTATCVALFAVGVAGNLLTVLVVRRFRELRTTTN
LYLCSLACSDLLIFLCMPLDLVRLWQYRPWTFGDLLCKLFQFVSEGCTYATVLTITALSVERYF
AICFPLRAKVLVTKGRVKLALLAIWAVAFCSAGPIFVLVGVEHENGTDPRDTRECRATEFAVRS
GLLTAMVWVSSVFFLPVFCLTVLYGLIGRKLWRRGRGDTAGGASLREQSHRQTVKMLAVVV
FAFIFCWLPFHVGRYLFSKSFEPGSLEIAQISQYCNLVSFVLFYLSAAINPILYNIMSKKYRVAVF
KLLGFEPFSQRKLSTLKDESSRAWTESSINT (SEQ. ID. NO. :2)

FIG.2

```
huGHS-R    1   MWNATPSEEPGFNLTLADLDWDASPGNDSLGDEL   34
ratGHS-R   1   MWNATPSEEPEPNMTL-DLDWDASPGNDSLPDEL   33
swGHS-R    1   MWNATPSEEPGPNLTLPDLGWDAPPENDSLVEEL   34
dogGHS-R   1   MRNATAREGPGSA-----GWD-------------L  17 huGHS-R    35  LQLFPAPLLAGVTATCVALFVVGIAGNLLTMLVV   68
ratGHS-R   34  LPLFPAPLLAGVTATCVALFVVGISGNLLTMLVV   67
swGHS-R    35  LPLFPTPLLAGVTATCVALFVVGIAGNLLTMLVV   68
dogGHS-R   18  LPLFPAPLLAGVTATCVALFAVGMAGNLLTMLVV   51 huGHS-R    69  SRFRELRTTTNLYLSSMAFSDLLIFLCMPLDLVR   102
ratGHS-R   68  SRFRELRTTTNLYLSSMAFSDLLIFLCMPLDLVR   101
swGHS-R    69  SRFREMRTTTNLYLSSMAFSDLLIFLCMPLDLFR   102
dogGHS-R   52  RRFRELRTTTNLYLCSLACSDLLIFLCMPLDLVR   85 huGHS-R    103 LWQYRPWNFGDLLCKLFQFVSESCTYATVLTITA   136
ratGHS-R   102 LWQYRPWNFGDLLCKLFQFVSESCTYATVLTITA   135
swGHS-R    103 LWQYRPWNLGNLLCKLFQFVSESCTYATVLTITA   136
dogGHS-R   86  LWQYRPWTFGDLLCKLFQFVSEGCTYATVLTITA   119 huGHS-R    137 LSVERYFAICFPLRAKVVVTKGRVKLVIFVIWAV   170
ratGHS-R   136 LSVERYFAICFPLRAKVVVTKGRVKLVILVIWAV   169
swGHS-R    137 LSVERYFAICFPLRAKVVVTKGRVKLVILVIWAV   170
dogGHS-R   120 LSVERYFAICFPLRAKVLVTKGRVKLALLAIWAV   153 huGHS-R    171 AFCSAGPIFVLVGVEHENGTDPWDTNECRPTEFA   204
ratGHS-R   170 AFCSAGPIFVLVGVEHENGTDPRDTNECRATEFA   203
swGHS-R    171 AFCSAGPIFVLVGVEHDNGTDPRDTNECRATEFA   204
dogGHS-R   154 AFCSAGPIFVLVGVEHENGTDPRDTRECRATEFA   187
```

FIG. 3A

```
huGHS-R  205  VRSGLLTVMVWVSSIFFFLPVFCLTVLYSLIGRK  238
ratGHS-R 204  VRSGLLTVMVWVSSVFFFLPVFCLTVLYSLIGRK  237
swGHS-R  205  VRSGLLTVMVWVSSVFFFLPVFCLTVLYSLIGRK  238
dogGHS-R 188  VRSGLLTAMVWVSSVFFFLPVFCLTVLYGLIGRK  221 huGHS-R  239  LWRRRRGDAVVGASLRDQNHKQTVKMLAVVVFAF  272
ratGHS-R 238  LWRRR-GDAAVGASLRDQNHKQTVKMLAVVVFAF  270
swGHS-R  239  LWRRKRGEAAVGSSLRDQNHKQTVKMLAVVVFAF  272
dogGHS-R 222  LWRRGRGDTAGGASLREQSHRQTVKMLAVVVFAF  255 huGHS-R  273  ILCWLPFHVGRYLFSKSFEPGSLEIAQISQYCNL  308
ratGHS-R 271  ILCWLPFHVGRYLFSKSFEPGSLEIAQISQYCNL  304
swGHS-R  273  ILCWLPFHVGRYLFSKSLEPGSVEIAQISQYCNL  306
dogGHS-R 256  IFCWLPFHVGRYLFSKSFEPGSLEIAQISQYCNL  289 huGHS-R  307  VSFVLFYLSAAINPILYNIMSKKYRVAVFRLLGF  340
ratGHS-R 305  VSFVLFYLSAAINPILYNIMSKKYRVAVFKLLGF  338
swGHS-R  307  VSFVLFYLSAAINPILYNIMSKKYRVAVFKLLGF  340
dogGHS-R 290  VSFVLFYLSAAINPILYNIMSKKYRVAVFKLLGF  323 huGHS-R  341  EPFSQRKLSTLKDESSRAWTESSINT  366
ratGHS-R 339  ESFSQRKLSTLKDESSRAWTKSSINT  364
swGHS-R  341  EPFSQRKLSTLKDESSRAWTESSINT  366
dogGHS-R 324  EPFSQRKLSTLKDESSRAWTESSINT  349
```

FIG. 3B

CANINE GROWTH HORMONE SECRETAGOGUE RECEPTOR

This application claims the benefit of Provisional application Ser. No. 60/095,960, filed Aug. 10, 1998.

CROSS-REFERENCE TO RELATED APPLICATIONS

Not applicable.

STATEMENT REGARDING FEDERALLY-SPONSORED R&D

Not applicable.

REFERENCE TO MICROFICHE APPENDIX

Not applicable.

FIELD OF THE INVENTION

The present invention is directed to a novel canine DNA sequence encoding the canine growth hormone secretagogue receptor as well as to the protein encoded by that DNA.

BACKGROUND OF THE INVENTION

Growth hormone (GH) is an anabolic hormone capable of promoting linear growth, weight gain and whole body nitrogen retention in mammals. GH is thought to be released primarily from the somatotroph cells of the anterior pituitary. under the coordinate regulation of two hypothalamic hormones, growth hormone releasing factor (GHRF or GRF) and somatostatin. Both GHRF stimulation and somatostatin inhibition of the release of GH occurs by the specific engagement of receptors on the cell membrane of the somatotroph.

GH release is also stimulated by a group of short peptides known as growth hormone releasing peptides (GHRPs) or as growth hormone secretagogues. Among the GHRPs are GHRP-2 (hexarelin) and GHRP-6, which are described, for example, in U.S. Pat. No. 4,411,890, PCT Patent Pub. No. WO 89/07110, PCT Patent Pub. No. WO 89/07111, PCT Patent Pub. No. WO 93/04081, and *J. Endocrinol Invest.*, 15 (Suppl 4), 45 (1992). GHRPs function by selectively binding to distinct somatotroph cell membrane receptor(s), the growth hormone secretagogue receptor(s) (GHSRs). A medicinal chemical approach has resulted in the design of several classes of orally-active, low molecular weight, non-peptidyl compounds which bind specifically to human GHSRs and result in the pulsatile release of GH. Such compounds possessing growth hormone secretagogue activity are disclosed, for example, in the following: U.S. Pat. No. 3,239,345; U.S. Pat. No. 4,036,979; U.S. Pat. No. 4,411,890; U.S. Pat. No. 5,206,235; and U.S. Pat. No. 5,283,241.

The use of orally-active agents which engage GHSRs and thus stimulate the pulsatile release of GH has been a significant advance in the treatment of growth hormone deficiency in children and adults and provides substantial benefit under circumstances where the anabolic effects of GH can be exploited clinically (e.g., post-hip fracture rehabilitation, the frail elderly, and in post-operative recovery patients). Other uses for such agents are being discovered from time to time. For example, Copinschi et al. 1997, Neuroendocrinol. 66:278–286 indicates that treatment with the non-peptidyl growth hormone secretagogue MK-677 improves sleep quality.

Provision of GHSRs from non-human species would allow for the development of a new set of agents that could be used as veterinary pharmaceuticals in animal disease states analagous to those described above for humans.

SUMMARY OF THE INVENTION

The present invention is directed to a novel canine DNA that encodes the canine growth hormone secretagogue receptor (GHSR). The DNA encoding canine GHSR is substantially free from other nucleic acids and has the nucleotide sequence shown in SEQ.ID.NO.:1. Also provided is a canine GHSR protein encoded by the novel DNA sequence. The canine GHSR protein is substantially free from other proteins and has the amino acid sequence shown in SEQ.ID.NO.:2. Methods of expressing the canine GHSR protein in recombinant systems and of identifying agonists and antagonists of the canine GHSR are provided.

BRIEF DESCRIPTION OF THE DRAWINGS

FIG. 1 shows a cDNA sequence encoding canine growth hormone secretagogue receptor (GHSR) (SEQ.ID.NO.:1). The sequence shown begins with the ATG start codon and ends with the TGA stop codon.

FIG. 2 shows the amino acid sequence of canine GHSR (SEQ.ID.NO.:2).

FIGS. 3A and 3B shows a comparison of the amino acid sequences of the human (SEQ.ID.NO.:5), rat (SEQ.ID.NO.:6), swine (SEQ.ID.NO.:7), and canine (SEQ.ID.NO.:2) GHSRs.

DETAILED DESCRIPTION OF THE INVENTION

For the purposes of this invention:

"Substantially free from other proteins" means at least 90%, preferably 95%, more preferably 99%, and even more preferably 99.9%, free of other proteins. Thus, a canine GHSR protein preparation that is substantially free from other proteins will contain, as a percent of its total protein, no more than 10%, preferably no more than 5%, more preferably no more than 1%, and even more preferably no more than 0.1%, of non-canine GHSR proteins. Whether a given canine GHSR protein preparation is substantially free from other proteins can be determined by such conventional techniques of assessing protein purity as, e.g., sodium dodecyl sulfate polyacrylamide gel electrophoresis (SDS-PAGE) combined with appropriate detection methods, e.g., silver staining or immunoblotting.

"Substantially free from other nucleic acids" means at least 90%, preferably 95%, more preferably 99%, and even more preferably 99.9%, free of other nucleic acids. Thus, a canine GHSR DNA preparation that is substantially free from other nucleic acids will contain, as a percent of its total nucleic acid, no more than 10%, preferably no more than 5%, more preferably no more than 1%, and even more preferably no more than 0.1%, of non-canine GHSR nucleic acids. Whether a given canine GHSR DNA preparation is substantially free from other nucleic acids can be determined by such conventional techniques of assessing nucleic acid purity as, e.g., agarose gel electrophoresis combined with appropriate staining methods, e.g., ethidium bromide staining, or by sequencing.

A polypeptide has "substantially the same biological activity" as canine GHSR protein if that polypeptide has a $K_d$ for a ligand of canine GHSR protein such as, e.g., MK-677, GHRP-6, L-692,429, that is no more than 5-fold greater than the $K_d$ of canine GHSR protein having the amino acid sequence of SEQ.ID.NO.:2 for the same ligand.

A "conservative amino acid substitution" refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid); substitution of one aromatic amino acid (tryptophan, tyrosine, or phenylalanine) for another.

The present invention relates to the identification and cloning of a cDNA encoding the canine GHSR. The present invention includes DNA molecules substantially free from other nucleic acids comprising SEQ.ID.NO.:1.

The novel DNA sequences of the present invention encoding canine GHSR, in whole or in part, can be linked with other DNA sequences, i.e., DNA sequences to which cDNA encoding canine GHSR is not naturally linked, to form "recombinant DNA molecules" encoding canine GHSR. Such other sequences can include DNA sequences that control transcription or translation such as, e.g., translation initiation sequences, promoters for RNA polymerase II, transcription or translation termination sequences, enhancer sequences, sequences that control replication in microorganisms, sequences that confer antibiotic resistance, or sequences that encode a polypeptide "tag" such as, e.g., a polyhistidine tract or the myc epitope. The novel DNA sequences of the present invention can be inserted into vectors such as plasmids, cosmids, viral vectors, P1 artificial chromosomes, or yeast artificial chromosomes. Accordingly, the present invention includes recombinant DNA molecules comprising SEQ.ID.NO.:1.

Included in the present invention are DNA sequences that hybridize to SEQ.ID.NO.:1 under stringent conditions. By way of example, and not limitation, a procedure using conditions of high stringency is as follows: Prehybridization of filters containing DNA is carried out for 2 hr. to overnight at 65° C. in buffer composed of 6×SSC, 5×Denhardt's solution, and 100 µg/ml denatured salmon sperm DNA. Filters are hybridized for 12 to 48 hrs at 65° C. in prehybridization mixture containing 100 µg/ml denatured salmon sperm DNA and 5–20×10$^6$ cpm of $^{32}$P-labeled probe. Washing of filters is done at 37° C. for 1 hr in a solution containing 2×SSC, 0.1% SDS. This is followed by a wash in 0.1×SSC, 0.1% SDS at 50° C. for 45 min. before autoradiography.

Other procedures using conditions of high stringency would include either a hybridization carried out in 5×SSC, 5×Denhardt's solution, 50% formamide at 42° C. for 12 to 48 hours or a washing step carried out in 0.2×SSPE, 0.2% SDS at 65° C. for 30 to 60 minutes.

Reagents mentioned in the foregoing procedures for carrying out high stringency hybridization are well known in the art. Details of the composition of these reagents can be found in, eg., Sambrook, Fritsch, and Maniatis, 1989, *Molecular Cloning: A Laboratory Manual*, second edition, Cold Spring Harbor Laboratory Press. In addition to the foregoing, other conditions of high stringency which may be used are well known in the art.

The degeneracy of the genetic code is such that, for all but two amino acids, more than a single codon encodes a particular amino acid. This allows for the construction of synthetic DNA that encodes the canine GHSR protein where the nucleotide sequence of the synthetic DNA differs significantly from the nucleotide sequence of SEQ.ID.NO.:1, but still encodes the same canine GHSR protein as SEQ.ID.NO.:1. Such synthetic DNAs are intended to be within the scope of the present invention.

Other DNA sequences included in the present invention are those DNA sequences that are identical to SEQ.ID.NO.:1 except that the last three nucleotides (TGA, the stop codon) differ. In particular, the stop codon of SEQ.ID.NO.:1 can be replaced by other stop codons (TAA or TAG).

Another aspect of the present invention includes host cells that have been engineered to contain and/or express DNA sequences encoding canine GHSR protein. Such recombinant host cells can be cultured under suitable conditions to produce canine GHSR protein. An expression vector containing DNA encoding canine GHSR protein can be used for expression of canine GHSR protein in a recombinant host cell. Recombinant host cells may be prokaryotic or eukaryotic, including but not limited to, bacteria such as *E. coli*, fungal cells such as yeast, mammalian cells including, but not limited to, cell lines of human, bovine, porcine, monkey and rodent origin, and insect cells including but not limited to Drosophila and silkworm derived cell lines. Cell lines derived from mammalian species which are suitable for recombinant expression of canine GHSR protein and which are commercially available, include but are not limited to, L cells L-M(TK$^-$) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

A variety of mammalian expression vectors can be used to express recombinant canine GHSR in mammalian cells. Commercially available mammalian expression vectors which are suitable include, but are not limited to, pMC1neo (Stratagene), pSG5 (Stratagene), pcDNAI and pcDNAIamp, pcDNA3, pcDNA3.1, pCR3.1 (Invitrogen), EBO-pSV2-neo (ATCC 37593), pBPV-1(8-2) (ATCC 37110), pdBPV-MMTneo(342-12) (ATCC 37224), pRSVgpt (ATCC 37199), pRSVneo (ATCC 37198), and pSV2-dhfr (ATCC 37146). Following expression in recombinant cells, canine GHSR protein can be purified by conventional techniques to a level that is substantially free from other proteins.

The present invention includes canine GHSR protein substantially free from other proteins. The amino acid sequence of the full-length canine GHSR protein is shown in FIG. 2 as SEQ.ID.NO.:2. Thus, the present invention includes canine GHSR protein substantially free from other proteins having the amino acid sequence of SEQ.ID.NO.:2.

The amino acid sequence of the canine GHSR protein (SEQ.ID.NO.:2) indicates that the canine GHSR protein contains many of the characteristic features of G-protein coupled receptors (GPCRs):

(a) seven transmembrane domains;

b) three intracellular loops;

(c) three extracellular loops; and (d) the GPCR triplet signature sequence.

As with many proteins, it is possible to modify many of the amino acids of canine GHSR and still retain substantially the same biological activity as the original protein. Thus, the present invention includes modified canine GHSR proteins which have amino acid deletions, additions, or substitutions but that still retain substantially the same biological activity as canine GHSR. It is generally accepted that single amino acid substitutions do not usually alter the biological activity of a protein (see, erg., *Molecular Biology of the Gene*, Watson et al., 1987, Fourth Ed., The Benjamin/Cummings Publishing Co., Inc., page 226; and Cunningham & Wells, 1989, Science 244:1081–1085). Accordingly, the present invention includes polypeptides where one amino acid substitution has been made in SEQ.ID.NO.:2 wherein the polypeptides still retain substantially the same biological activity as canine GHSR protein. The present invention also includes polypeptides where two or more amino acid substitutions have been made in SEQ.ID.NO.:2 wherein the polypeptides still retain substantially the same biological activity as canine GHSR protein. In particular, the present invention includes canine GHSR polypeptides containing two or more amino acid substitutions where the substitutions do not occur in positions where all four of the human, rat, swine, and canine GHSRs share the same amino acid (see FIG. 3) and where the protein has substantially the same biological activity as canine GHSR having the amino acid sequence SEQ.ID.NO.:2. In particular, the present invention includes embodiments where the above-described substitutions are conservative substitutions. In particular, the present invention includes embodiments where the above-described substitutions do not occur in the ligand binding domain.

The canine GHSR proteins of the present invention may contain post-translational modifications, e.g., covalently linked carbohydrate, phosphorylated tyrosine.

The present invention also includes chimeric canine GHSR proteins. Chimeric canine GHSR proteins consist of a contiguous polypeptide sequence of at least a portion of a canine GHSR protein fused to a polypeptide sequence of a non-canine GHSR protein. For example, the N-terminal domain and seven transmembrane spanning domains of canine GHSR protein fused at the C-terminus in frame to a G protein would be a chimeric canine GHSR protein.

The present invention also includes canine GHSR proteins that are in the form of multimeric structures, e.g., dimers. Such multimers of other G-protein coupled receptors are known (Hebert et al., 1996, J. Biol. Chem. 271, 16384–16392; Ng et al., 1996, Biochem. Biophys. Res. Comm. 227, 200–204; Romano et al., 1996, J. Biol. Chem. 271, 28612–28616).

The present invention also includes isolated forms of canine GHSR proteins. By "isolated canine GHSR protein" is meant canine GHSR protein that has been isolated from a natural source. Use of the term "isolated" indicates that canine GHSR protein has been removed from its normal cellular environment. Thus, an isolated canine GHSR protein may be in a cell-free solution or placed in a different cellular environment from that in which it occurs naturally. The term isolated does not imply that an isolated canine GHSR protein is the only protein present. but instead means that an isolated canine GHSR protein is at least 95% free of non-amino acid material (e.g., nucleic acids, lipids, carbohydrates) naturally associated with the canine GHSR protein. Thus, a canine GHSR protein that is expressed through recombinant means in bacteria or even in eukaryotic cells which do not naturally (i.e., without human intervention) express it is an "isolated canine GHSR protein."

A cDNA fragment encoding full-length canine GHSR protein can be isolated from a canine cDNA library constructed from poly (A)+mRNA frm hypothalamus or pituitary gland by using the polymerase chain reaction (PCR) employing suitable primer pairs. Such primer pairs can be selected based upon the cDNA sequence for canine GHSR shown in FIG. 1 as SEQ.ID.NO.:1. Suitable primer pairs would be, e.g.:

ATGCGGAACGCGACGGCC (SEQ.ID.NO.:3) and
TCATGTATAATACTTAG (SEQ.ID.NO.:4).

The above-described primers will allow for the amplification of the complete cDNA. These primers are meant to be illustrative. Other suitable primers will be evident to those skilled in the art.

PCR reactions can be carried out with a variety of thermostable enzymes including but not limited to AMPLITAQ, AMPLITAQ GOLD, or Vent polymerase. For AMPLITAQ, reactions can be carried out in 10 mM Tris-Cl, pH 8.3, 2.0 mM $MgCl_2$, 200 $\mu$M for each dNTP, 50 mM KCl, 0.2 $\mu$M for each primer, 10 ng of DNA template, 0.05 units/$\mu$l of AMPLITAQ. The reactions are heated at 95° C. for 3 minutes and then cycled 35 times using the cycling parameters of 95° C., 20 seconds, 62° C. 20 seconds, 72° C., 3 minutes. In addition to these conditions, a variety of suitable PCR protocols can be found in *PCR Primer, A Laboratory Manual*, edited by C. W. Dieffenbach and G. S. Dveksler, 1995, Cold Spring Harbor Laboratory Press; or *PCR Protocols: A Guide to Methods and Applications*, Michael et al., eds., 1990, Academic Press.

A suitable cDNA library from which a clone encoding canine GHSR can be isolated from a cDNA library constructed from canine hypothalamic poly (A)+mRNA that has been cloned into a suitable vector, e.g., the vector pcDNA-3.1 (Invitrogen, San Diego, Calif.) by methods well-known in the art. The primary clones of such a library can be subdivided into pools with each pool containing approximately 20,000 clones and each pool can be amplified separately.

By this method, a cDNA fragment encoding an open reading frame of 349 amino acids (SEQ.ID.NO.:2) can be obtained. This cDNA fragment can be cloned into a suitable cloning vector or expression vector. For example, the fragment can be cloned into the mammalian expression vector pcDNA3.1 (Invitrogen, San Diego, Calif.). Canine GHSR protein can then be produced by transferring an expression vector encoding canine GHSR or portions thereof into a suitable host cell and growing the host cell under appropriate conditions. Canine GHSR protein can then be isolated by methods well known in the art.

As an alternative to the above-described PCR method, a cDNA clone encoding canine GHSR protein can be isolated from a cDNA library using as a probe oligonucleotides specific for canine GHSR and methods well known in the art for screening cDNA libraries with oligonucleotide probes. Such methods are described in, e.g., Sambrook et al., 1989, *Molecular Cloning. A Laboratory Manual*; Cold Spring Harbor Laboratory, Cold Spring Harbor, N.Y.; Glover, D. M. (ed.), 1985, *DNA Cloning: A Practical Approach*, MRL Press, Ltd., Oxford, U.K., Vol. I, II. Oligonucleotides that are specific for canine GHSR and that can be used to screen cDNA libraries can be readily designed based upon the cDNA sequence of canine GHSR shown in FIG. 1 as SEQ.ID.NO.:1 and can be synthesized by methods well-known in the art.

Genomic clones containing the canine GHSR gene can be obtained from commercially available canine genomic libraries such as the canine lambda genomic DNA library from Stratagene (catalog number 946802). Alternatively, one may prepare canine genomic libraries, especially in P1 artificial chromosome vectors, from which genomic clones containing the canine GHSR can be isolated, using probes based upon the canine GHSR sequences disclosed herein. Methods of preparing such libraries are known in the art (Ioannou et al., 1994, Nature Genet. 6:84–89).

The present invention also provides oligonucleotides, based upon SEQ.ID.NO.:1, that can be used to isolate the canine GHSR-gene or to isolate GHSR genes from other species. In particular, the present invention includes DNA oligonucleotides comprising at least 18 contiguous nucleotides of SEQ.ID.NO.:1. Also provided by the present invention are corresponding RNA oligonucleotides. The DNA or RNA oligonucleotides can be packaged in kits.

The present invention makes possible the recombinant expression of the canine GHSR protein in various cell types. Such recombinant expression makes possible the study of this protein so that its biochemical mechanism of action and its physiological role can be elucidated. Accordingly, the present invention includes a method of expressing canine GHSR protein comprising:

(a) transfecting host cells with an expression vector that encodes canine GHSR protein;

(b) culturing the transfected cells of step (a) under conditions such that canine GHSR protein is expressed.

In particular embodiments, the cells are eukaryotic cells. In other embodiments, the cells are mammalian cells. In still other embodiments, the cells are COS cells, in particular COS-7 cells (ATCC CRL 1651), or melanophores.

The present invention also includes C-terminal truncated forms of canine GHSR protein, particularly those which encompass the extracellular portion of the receptor, but lack the intracellular signaling portion of the receptor. Such truncated receptors are useful in various binding assays described herein, for crystallization studies, and for structure-activity-relationship studies.

It has been found that, in some cases, membrane spanning regions of receptor proteins can be used to inhibit receptor function (Ng et al., 1996, Biochem. Biophys. Res. Comm. 227:200–204; Hebert et al., 1996, J. Biol. Chem. 271, 16384–16392; Lofts et al., Oncogene 8:2813–2820). Accordingly, the present invention provides peptides derived from the seven membrane spanning regions of canine GHSR protein and their use to inhibit canine GHSR function. Such peptides can include the whole or parts of the receptor membrane spanning domains.

The present invention makes possible the development of assays which measure the biological activity of the canine GHSR protein. Such assays using recombinantly expressed canine GHSR protein are especially of interest. Assays for canine GHSR protein activity can be used to screen libraries of compounds or other sources of compounds to identify compounds that are activators or inhibitors of the activity of canine GHSR protein. Such identified compounds can serve as "leads" for the development of veterinary pharmaceuticals that can be used to treat dogs having illnesses in which inappropriate activity of the canine GHSR protein is involved. In versions of the above-described assays, mutant canine GHSR proteins are used and inhibitors or activators of the activity of the mutant canine GHSR proteins are discovered.

In general, such assays comprise:

(a) recombinantly expressing canine GHSR protein or mutant canine GHSR protein in a host cell;

(b) measuring the biological activity of canine GHSR protein or mutant canine GHSR protein in the presence and in the absence of a substance suspected of being an activator or an inhibitor of canine GHSR protein or mutant canine GHSR protein;

where a change in the biological activity of the canine GHSR protein or the mutant canine GHSR protein in the presence as compared to the absence of the substance indicates that the substance is an activator or an inhibitor of canine GHSR protein or mutant canine GHSR protein.

The biological activity of the canine GHSR protein can be measured by measuring various changes in the host cells, e.g., an increase in intracellular calcium; depolarization and inhibition of potassium channels; increase in inositol triphosphate concentration; or an increase in the activity of protein kinase C (Howard et al., 1996, Science 273:974–977).

Using the CDNA provided by the present invention (SEQ.ID.NO.:1) and methods well-known in the art, complementary RNA (cRNA) can be prepared encoding the canine GHSR protein. This cRNA can be injected into Xeztopus oocytes in order to cause the expression of canine GHSR protein in the oocytes. The oocytes can then be exposed to substances suspected of being agonists of the canine GHSR protein. If the substance is actually an agonist, it will cause oscillatory increases in calcium activated chloride currents. In this manner, agonists of the canine GHSR can be identified. To improve the sensitivity of this assay, the oocytes can be injected with cRNA encoding the bioluminescent $Ca^{2+}$ sensitive protein aequorin and cRNA encoding a $G\alpha$ subunit (e.g., $G\alpha 11$) in addition to being injected with cRNA encoding canine GHSR protein. Such methods of assaying for agonists of other GPCRs are known in the art (see, e.g., Howard et al., 1996, Science 273:974–977).

The specificity of binding of compounds having affinity for canine GHSR protein can be shown by measuring the affinity of the compounds for recombinant cells expressing the cloned receptor or for membranes from these cells. Expression of the cloned. receptor and screening for compounds that bind to canine GHSR or that inhibit the binding of a known, labeled ligand of canine GHSR to these cells, or membranes prepared from these cells, provides an effective method for the rapid selection of compounds with high affinity for canine GHSR. The compounds need not necessarily be labeled but can be non-labeled compounds that can be used to displace bound labeled compounds or that can be used as activators in functional assays. Those compounds identified by the above method are likely to be agonists or antagonists of canine GHSR and may be peptides, proteins, or non-proteinaceous organic molecules.

Therefore, the present invention includes assays by which canine GHSR agonists and antagonists may be identified. Analogous methods for identifying agonists and antagonists of other receptors are well known in the art and can be adapted to identify agonists and antagonists of canine GHSR. For example, Cascieri et al., 1992, Molec. Pharmacol. 41:1096–1099 describe a method for identifying substances that inhibit agonist binding to rat neurokinin receptors and thus are potential agonists or antagonists of neurokinin receptors. The method involves transfecting COS cells with expression vectors containing rat neurokinin receptors, allowing the transfected cells to grow for a time sufficient to allow the neurokinin receptors to be expressed, harvesting the transfected cells and resuspending the cells in assay buffer containing a known radioactively labeled agonist of the neurokinin receptors either in the presence or the absence of the substance, and then measuring the binding of the radioactively labeled known agonist of the neurokinin receptor to the neurokinin receptor. If the amount of binding of the known agonist is less in the presence of the substance than in the absence of the substance, then the substance is a potential agonist or antagonist of the neurokinin receptor.

Accordingly, the present invention includes a method for determining whether a substance is a potential agonist or antagonist of canine GHSR that comprises:

(a) transfecting cells with an expression vector encoding canine GHSR;

(b) allowing the transfected cells to grow for a time sufficient to allow canine GHSR to be expressed;

(c) harvesting the transfected cells and resuspending the cells in the presence of a known labeled agonist of the canine GHSR in the presence and in the absence of the substance;

(d) measuring the binding of the labeled agonist to canine GHSR; where if the amount of binding of the known agonist is less in the presence of the substance than in the absence of the substance, then the substance is a potential agonist or antagonist of canine GHSR.

In a modification of the above-described method, step (b) is modified in that the cells are stably transfected with the expression vector containing canine GHSR. In another modification of the above-described method, step (c) is modified in that the cells are not harvested and resuspended but rather the radioactively labeled known agonist and the substance are contacted with the cells while the cells are attached to a substratum, e.g., tissue culture plates.

The conditions under which step (c) of the above-described method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C.

The present invention also includes a method for determining whether a substance is capable of binding to canine GHSR. i.e., whether the substance is a potential agonist or an antagonist of canine GHSR, where the method comprises:

(a) providing test cells by transfecting cells with an expression vector that directs the expression of canine GHSR in the cells;

(b) exposing the test cells to the substance;

(c) measuring the amount of binding of the substance to canine GHSR in the test cells;

(d) comparing the amount of binding of the substance to canine GHSR in the test cells with the amount of binding of the substance to the same cells that have not been transfected with canine GHSR.

Where the amount of binding of the substance is greater in the test cells as compared to the control cells, the substance is capable of binding to canine GHSR and thus is a likely agonist or antagonist of canine GHSR. Determining whether the substance is actually an agonist or antagonist can then be accomplished by the use of functional assays such as, e.g., the Xenopus oocyte assay described above and in Howard et al., 1996, Science 273:974–977 or the assay involving the use of promiscuous G-proteins described below.

The conditions under which step (b) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C.

In a modification of the above method, the present invention includes a method for determining whether a substance is capable of binding to canine GHSR comprising:

(a) providing test cells by transfecting cells with an expression vector that directs the expression of canine GHSR in the cells;

(b) exposing the test cells to a known ligand of canine GHSR under conditions such that the known ligand of canine GHSR binds to the canine GHSR in the test cells;

(c) subsequently or concurrently to step (b), exposing the test cells to a substance that is suspected of being capable of binding to canine GHSR;

(d) measuring the amount of binding of the known ligand of canine GHSR to canine GHSR in the presence and the absence of the substance;

(e) comparing the amount of binding of the known ligand of canine GHSR to canine GHSR in the presence and the absence of the substance where a decrease in the amount of binding of the known ligand of canine GHSR to canine GHSR in the presence of the substance indicates that the substance is capable of binding to canine GHSR.

The assays described above can be carried out with cells that have been transiently or stably transfected with canine GHSR. Transfection is meant to include any method known in the art for introducing canine GHSR into the test cells. For example, transfection includes calcium phosphate or calcium chloride mediated transfection, lipofection, infection with a retroviral construct containing canine GHSR, and electroporation.

Where binding of the substance or agonist to canine GHSR is measured, such binding can be measured by employing a labeled substance or agonist. The substance or agonist can be labeled in any convenient manner known to the art, e.g., radioactively, fluorescently, enzymatically. Similarly, binding of a known ligand of canine GHSR to canine GHSR can be measured by employing a known ligand of canine GHSR that has been labeled. Known ligands of canine GHSR can be chosen from among the group of known ligands for human, rat, or swine GHSRs.

The above-described methods can be modified in that, rather than exposing the test cells to the substance, membranes can be prepared from the test cells and those membranes can be exposed to the substance. Such a modification utilizing membranes rather than cells is well known in the art and is described in, e.g., Hess et al., 1992, Biochem. Biophys. Res. Comm. 184:260–268.

In particular embodiments of the above-described methods, canine GHSR has the amino acid sequence shown in SEQ.ID.NO.:2.

In particular embodiments of the above-described methods, the expression vector comprises SEQ.ID.NO.:1.

In a particular embodiment of the above-described methods, the cells are eukaryotic cells. In another embodiment, the cells are mammalian cells. In other embodiments, the cells are L cells L-M(TK−) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) or MRC-5 (ATCC CCL 171).

The present invention includes assays by which canine GHSR agonists and antagonists maybe identified by their ability to stimulate or antagonize a functional response mediated by canine GHSR. Canine GHSR belongs to the class of proteins known as G-protein coupled receptors (GPCRs). GPCRs transmit signals across cell membranes upon the binding of ligand. The ligand-bound GPCR interacts with a heterotrimeric G-protein, causing the Gα subunit of the G-protein to disassociate from the Gβ and Gγ subunits. The Gα subunit (and sometimes the Gβ and Gγ subunits) can then go on to activate a variety of second messenger systems.

There are many types of G-proteins, with many types of subunits. Generally, a particular GPCR is only coupled to a particular type of G-protein. Thus, to observe a functional response from the GPCR, it is usually necessary to ensure that the proper G-protein is present in the system containing the GPCR. It has been found, however, that there are certain G-proteins that are "promiscuous." These promiscuous G-proteins will couple to, and thus transduce a functional signal from, virtually any GPCR. See Offermanns & Simon, 1995, J. Biol. Chem. 270:15175, 15180 (Offermanns). Offermanns described a system in which cells are transfected with expression vectors that result in the expression of one of a large number of GPCRs as well as the expression of one of the promiscuous G-proteins Gα15 or Gα16. Upon the addition of an agonist of the GPCR to the transfected cells, the GPCR was activated and was able, via Gα15 or Gα16, to activate the β isoform of phospholipase C, leading to an increase in inositol phosphate levels in the cells.

Since canine GHSR functions in the aequorin assay, it is likely to be coupled through Gαq11. Thus, one could set up functional assays for canine GHSR by transfecting cells with an expression vector encoding SEQ.ID.NO.:1 as well as an expression vector encoding Gαq11. Alternatively, by making use of these promiscuous G-proteins as in Offermanns, it is possible to set up functional assays for canine GHSR, even in the absence of knowledge of the G-protein with which canine GHSR is coupled in vivo. One possibility is to create a fusion or chimeric protein composed of the extracellular and membrane spanning portion of canine GHSR fused to a promiscuous G-protein. Such a fusion protein would be expected to transduce a signal following binding of ligand to the canine GHSR portion of the fusion protein. Accordingly, the present invention provides a method of identifying antagonists of canine GHSR comprising:

(a) providing cells that expresses a chimeric canine GHSR protein fused at its C-terminus to a promiscuous G-protein;

(b) exposing the cells to an agonist of canine GHSR;

(c) subsequently or concurrently to step (b), exposing the cells to a substance that is a suspected antagonist of canine GHSR;

(d) measuring the level of inositol phosphates in the cells;

where a decrease in the level of inositol phosphates in the cells in the presence of the substance as compared to the level of inositol phosphates in the cells in the absence of the substance indicates that the substance is an antagonist of canine GHSR.

Another possibility. for utilizing promiscuous G-proteins in connection with canine GHSR includes a method of identifying agonists of canine GHSR comprising:

(a) providing cells that expresses both canine GHSR and a promiscuous G-protein;

(b) exposing the cells to a substance that is a suspected agonist of canine GHSR;

(c) measuring the level of inositol phosphates in the cells;

where an increase in the level of inositol phosphates in the cells as compared to the level of inositol phosphates in the cells in the absence of the suspected agonist indicates that the substance is an agonist of canine GHSR.

Another possibility for utilizing promiscuous G-proteins in connection with canine GHSR includes a method of identifying agonists of canine GHSR comprising:

(a) providing test cells that expresses both canine GHSR and a promiscuous G-protein;

(b) providing control cells that are identical to the cells of step (a) except that the control cells do not express canine GHSR;

(c) exposing the test cells and the control cells to a substance that is a suspected agonist of canine GHSR;

(c) measuring the level of inositol phosphates in the test cells and the control cells;

where an increase in the level of inositol phosphates in the test cells as compared to the level of inositol phosphates in the control cells indicates that the substance is an agonist of canine GHSR.

Levels of inositol phosphates can be measured by monitoring calcium mobilization. Intracellular calcium mobilization is typically assayed in whole cells under a microscope using fluorescent dyes or in cell suspensions via luminescence using the aequorin assay.

In a particular embodiment of the above-described methods, the cells are eukaryotic cells. In another embodiment, the cells are mammalian cells. In other embodiments, the cells are L cells L-M(TK$^-$) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) or MRC-5 (ATCC CCL 171).

In a particular embodiment of the above-described methods, the cells are transfected with expression vectors that direct the expression of canine GHSR and the promiscuous G-protein in the cells.

The conditions under the cells are exposed to the substance are conditions that are typically used in the art for the study of protein-ligand interactions: e.g., physiological pH; salt conditions such as those represented by such commonly used buffers as PBS or in tissue culture media; a temperature of about 4° C. to about 55° C.

In a particular embodiment of the above-described methods, the promiscuous G-protein is selected from the group consisting of Gα15 or Gα16. Expression vectors containing Gα15 or Gα16 are known in the art. See, e.g., Offermanns; Buhl et al., 1993, FEBS Lett. 323:132–134; Amatruda et al., 1993, J. Biol. Chem. 268:10139–10144.

The above-described assay can be. easily modified to form a method to identify antagonists of canine GHSR. Such a method is also part of the present invention and comprises:

(a) providing cells that expresses both canine GHSR and a promiscuous G-protein;

(b) exposing the cells to a substance that is an agonist of canine GHSR;

(c) subsequently or concurrently to step (b), exposing the cells to a substance that is a suspected antagonist of canine GHSR;

(d) measuring the level of inositol phosphates in the cells;

where a decrease in the level of inositol phosphates in the cells in the presence of the suspected antagonist as compared to the level of inositol phosphates in the cells in the absence of the suspected antagonist indicates that the substance is an antagonist of canine GHSR.

In a particular embodiment of the above-described method, the cells are eukaryotic cells. In another embodiment, the cells are mammalian cells. In other embodiments, the cells are L cells L-M(TK$^-$) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The conditions under which steps (b) and (c) of the method are practiced are conditions that are typically used in the art for the study of protein-ligand interactions: e.g., physiological pH; salt conditions such as those represented by such commonly used buffers as PBS or in tissue culture media; a temperature of about 4° C. to about 55° C.

In a particular embodiment of the above-described method, the cells are transfected with expression vectors that direct the expression of canine GHSR and the promiscuous G-protein in the cells.

In a particular embodiment of the above-described method, the promiscuous G-protein is selected from the group consisting of Gα15 or Gα16.

In particular embodiments of the above-described methods, canine GHSR has the amino acid shown in SEQ.ID.NO.:2.

While the above-described methods are explicitly directed to testing whether "a" substance is an activator or an inhibitor of canine GHSR, it will be clear to one skilled in the art that such methods can be adapted to test collections of substances, e.g., combinatorial libraries, to determine whether any members of such collections are activators or inhibitors of canine GHSR. Accordingly, the use of collections of substances as the substance in the above-described methods is within the scope of the present invention.

Given the wide range of utility displayed by known agonists and antagonists of human GHSRs, it is clear that those skilled in the art would consider the agonists and antagonists of canine GHSR identified by the methods of the present invention to be pharmacologically useful in a similar manner in canines. In addition to their use in canines, agonists and antagonists of canine GHSR identified by the above-described methods will be useful for guiding the choice of compounds with ideal pharmaceutical properties (e.g. oral bioavailability, duration of action) to be used in humans or other animal species (e.g. swine) for growth promoting effects.

When screening compounds in order to identify potential pharmaceuticals that specifically interact with a target receptor, it is necessary to ensure that the compounds identified are as specific as possible for the target receptor. To do this, it is necessary to screen the compounds against as wide an array as possible of receptors that are similar to the target receptor. Thus, in order to find compounds that are potential pharmaceuticals that interact with receptor A, it is necessary not only to ensure that the compounds interact with receptor A (the "plus target") and produce the desired pharmacological effect through receptor A, it is also necessary to determine that the compounds do not interact with receptors B, C, D, etc. (the "minus targets"). In general, as part of a screening program, it is important to have as many minus targets as possible (see Hodgson, 1992, Bio/Technology 10:973–980, at 980). Canine GHSR protein and DNA encoding canine GHSR protein have utility in that they can be used as "minus targets" in screens design to identify compounds that specifically interact with other G-protein coupled receptors.

The present invention also includes antibodies to the canine GHSR protein. Such antibodies may be polyclonal antibodies or monoclonal antibodies. The antibodies of the present invention are raised against the entire canine GHSR protein or against suitable antigenic fragments of the protein that are coupled to suitable carriers, e.g., serum albumin or keyhole limpet hemocyanin, by methods well known in the art. Methods of identifying suitable antigenic fragments of a protein are known in the art. See, e.g., Hopp & Woods, 1981, Proc. Natl. Acad. Sci. USA 78:3824–3828; and Jameson & Wolf, 1988, CABIOS (Computer Applications in the Biosciences) 4:181–186.

For the production of polyclonal antibodies, canine GHSR protein or an antigenic fragment, coupled to a suitable carrier, is injected on a periodic basis into an appropriate non-human host animal such as, e.g., rabbits, sheep, goats, rats, mice. The animals are bled periodically and sera obtained are tested for the presence of antibodies to the injected antigen. The injections can be intramuscular, intraperitoneal, subcutaneous, and the like, and can be accompanied with adjuvant.

For the production of monoclonal antibodies, canine GHSR protein or an antigenic fragment, coupled to a suitable carrier, is injected into an appropriate non-human host animal as above for the production of polyclonal antibodies. In the case of monoclonal antibodies, the animal is generally a mouse. The animal's spleen cells are then immortalized, often by fusion with a myeloma cell, as described in Kohler & Milstein, 1975, Nature 256:495–497. For a fuller description of the production of monoclonal antibodies, see Antibodies: A Laboratory Manual, Harlow & Lane, eds., Cold Spring Harbor Laboratory Press, 1988.

The following non-limiting examples are presented to better illustrate the invention.

EXAMPLE 1

Isolation of Full-length Genomic Clones for Canine GHSR

A commercially available canine spleen genomic library in lambda dash vector (Stratagene, La Jolla, Calif.) was employed for cloning of a dog GHSR type 1a and can be used to isolate other canine GHSR family members. Approximately $1.8 \times 10^6$ clones were plated and the plaques were then lifted onto NYTRAN extra strength filters (Schleicher & Schuell, Keene, N.H.) according to the manufacturer's specifications. The filters were pre-hybridized in 50% formamide, 5×SSPE, 2×Denhardt's, 0.1% SDS, 100 μg/ml salmon sperm DNA for 2 hrs at 30° C. followed by overnight hybridization at 30° C. in 50% formnamide, 5×SSPE, 2×Denhardt's, 0.1% SDS, 10% dextran sulfate, 100 μg/ml salmom sperm DNA. To identify positive clones, the open reading frame of human type 1a GHSR (1.1 kb) was random primed using Strategene Prime It II kit and added to hybridization solution at $1 \times 10^6$ cpm/ml. Posthybridization, the filters were washed in moderate stringency (1×SSC, 0.1% SDS at 55° C. for 30 min) and exposed to X-ray film. Three rounds of plaque purification revealed 5 positive clones (3, 19, 25, 27 and 28). Lambda phage liquid lysate preparation was performed according to a protocol supplied by Clontech labs. This DNA was digested with Sal I to generate 22 kb and 9 kb DNA fragments. For clone 19, the 22 kb insert which hybridized to human type 1a probe was subcloned into pGem 11 zf+Sal I site (Promega). Colony hybridization of approximately 1,000 transformants uncovered a single hybridizing subclone which was sequenced using the ABI prism FS dye terminator sequencing kit (Applied Biosystems, Foster City, Calif.). The other four clones were sequenced directly from the lambda DNA using newly available ABI prism FS bigdye terminator cycle sequencing kit.

EXAMPLE 2

Cloning of Canine cDNA for the GHSR

Dog hypothalamus mRNA was prepared from 1 g dog hypothalamus using the Poly(A) Pure mRNA isolation kit (Ambion Inc, Austin, Tex.) according to the manufacturer's instructions. cDNA was prepared from the mRNA using the Choice Superscript cDNA kit (BRL, Bethesda, Md.). After the column chromatography step, the cDNA was quantitated using DNA Dipstick (Invitrogen, Calif.). 10 ng cDNA was used as template for PCR using dog specific primers PCR1S (GGGCCC GAATTC GCC GCC ATG CGG AAC GCG ACG GCC CGC (SEQ.ID.NO.:8)) and PCR2AS (AGTTTA GCGG CCGC TCA TGT ATT AAT ACT AGA CTC TGT (SEQ.ID.NO.:9)). PCR reactions comprised 10 mM Tris (pH 8.0), 50 mM KCl, 1.5 mM $MgCl_2$, 100 μg/ml gelatin, 250 μM each dNTP, and 10% DMSO with 20 pmoles of each primer and 20 ng of target DNA. Prior to the addition of Taq polymerase (Pharmacia), the reactions were heated at 100° C. for 10 minutes followed by soaking at 72° C. Taq polymerase was added to a final concentration of 0.25 units/ml. The cycling parameters were 94° C. for 1 minute, 50° C. for 1 minute, 72° C. for 1 minute, for a total of 30 cycles, followed by incubation at 72° C. for 10 minutes. Reactions were electrophoresed on a 1% Seakem GTG agarose gel in 1×TAE buffer and visualized under long wave UV light. The fragment of expected size (1.2 kb) for the ORF (open reading frame) was electroeluted and TA cloned (Invitrogen, Calif.), sequenced with dye terminator cycle sequencing ready reactions (Perkin Elmer, Foster City, Calif.), and analyzed on a 377 ABI Prism cycle sequencer. The fragment was subcloned into the pCDNA3 vector for expression. Overall, the amino acid sequence (FIG. 3) of the cloned canine GHSR is 91% identical to the rat GHSR and 89% identical to the human GHSR. The most divergent feature of the canine GHSR compared to GHSR from other species is the absence of 17 amino acids in the N-terminal extracellular domain.

EXAMPLE 3

Radiolabeled MK-677 Binding Assay

Expression of the canine -GHSR was monitored using a [$^{35}$S]-MK-677 binding assay conducted on cells transfected with a canine GHSR expression plasmid (full-length open reading frame placed in the mammalian expression vector pcDNA-3). Mammalian cells (COS-7, HEK-293) were transfected with GHSR expression plasmids using Lipofectamine (GIBCO-BRL; Hawley-Nelson, 1993, Focus 15:73). Transfections were performed in 60 mm dishes on 80% confluent cells (approximately 4×10$^5$ cells) with 8 μg of Lipofectamine and 32 μg of GHSR plasmid DNA.

Binding of $^{35}$S-MK-677 to crude membranes prepared from COS-7 or HEK-293 cells transfected with GHSR expression plasmids was conducted. Crude cell membranes from COS-7 transfectants were prepared on ice, 48 hrs post-transfection. Each 60 mm dish was washed twice with 3 ml of PBS, once with 1 ml homogenization buffer (50 mM Tris-HCl (pH 7.4), 5 mM $MgCl_2$, 2.5 mM EDTA, 30 μg/ml bacitracin). 0.5 ml of homogenization buffer was added to each dish, cells were removed by scraping and then homogenized using a POLYTRON device (Brinkmann, Syosset, N.Y.; 3 bursts of 10 seconds at setting 4). The homegenate was then centrifuged for 20 minutes at 11,000×g at 0° C. and the resulting crude membrane pellet (chiefly containing cell membranes and nuclei) was resuspended in homogenization buffer supplemented with 0.06% BSA (0.1 ml/60 mm dish) and kept on ice. Binding reactions were performed at 20° C. for 1 hr in a total volume of 0.5 ml containing: 0.1 ml of membrane suspension, 10 μl of $^{35}$S-MK-677 (0.05 to 1 nM; specific activity approximately 900 Ci/mmol), 10 μl of competing drug, and 380–390 μl of homogenization buffer. Bound radioligand was separated by rapid vacuum filtration (Brandel 48-well cell harvester) through GF/C filters pretreated for 1 hr. with 0.5% polyethylenimine. After application of the membrane suspension to the filter, the filters were washed 3 times with 3 ml each of ice cold 50 mM Tris-HCl (pH 7.4), 10 mM $MgCl_2$, 2.5 mM-EDTA, and 0.015% Triton X-100, and the bound radioactivity on the filters was quantitated by scintillation counting. Specific binding (>90% of total) is defined as the difference between total binding and non-specific binding conducted in the presence of 50 nM unlabeled MK-677. Competition studies showed that the cloned canine GHSR binds MK-677 with an $IC_{50}$ value of 2.2 nM, which compares favorably to the native canine pituitary GHSR (1 nM) and cloned human GHSR (0.8 nM).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

---

What is claimed:

1. A recombinant DNA molecule encoding a polypeptide having the amino acid sequence SEQ.ID.NO.:2.

2. The recombinant DNA molecule of claim 1 comprising the nucleotide sequence SEQ.ID.NO.:1.

3. An expression vector comprising the DNA of claim 1.

4. A recombinant host cell comprising the expression vector of claim 3.

5. A method of expressing canine GHSR protein comprising:
   (a) transfecting host cells with an expression vector that encodes canine GHSR protein having the amino acid sequence SEQ.ID.NO.:2;
   (b) culturing the transfected cells of step (a) under conditions such that canine GHSR protein is expressed.

6. A method for identifying an activator or an inhibitor of canine GHSR protein, comprising:
   (a) recombinantly expressing canine GHSR protein having the amino acid sequence SEQ.ID.NO.:2 in a host cell;
   (b) measuring the biological activity of canine GHSR protein in the host cell in the presence and in the absence of a substance suspected of being an activator or an inhibitor of canine GHSR protein;
   where a change in the biological activity of the canine GHSR protein in the presence as compared to the absence of the substance indicates that the substance is an activator or an inhibitor of canine GHSR protein.

7. A method for determining whether a substance is a potential agonist or antagonist of canine GHSR that comprises:
   (a) transfecting cells with an expression vector encoding canine GHSR protein having the amino acid sequence SEQ.ID.NO.:2;
   (b) allowing the transfected cells to grow for a time sufficient to allow canine GHSR protein to be expressed;
   (c) exposing the transfected cells to a known labeled agonist of the canine GHSR in the presence and in the absence of the substance; and (d) measuring the binding of the labeled agonist to canine GHSR;

wherein if the amount of binding of the known agonist to canine GHSR is less in the presence of the substance than in the absence of the substance, then the substance is a potential agonist or antagonist of canine GHSR.

* * * * *

SEQUENCE LISTING

<160> NUMBER OF SEQ ID NOS: 9

<210> SEQ ID NO 1
<211> LENGTH: 1050
<212> TYPE: DNA
<213> ORGANISM: Canis familiaris
<220> FEATURE:
<221> NAME/KEY: misc_feature
<222> LOCATION: (1)...(1050)
<223> OTHER INFORMATION: n = A,T,C or G

<400> SEQUENCE: 1

```
atgcggaacg cgacggcccg cgagggcccg gggtcggcgg gctgggacct gctgccgctg      60
ttccccgcgc cgctgctggc gggcgtgacg gccacctgcg tggcgctgtt cgccgtgggc     120
gtcgcgggca acctgctgac ggtgctggtg gtgcggcgct ccgcgagct gcgcaccacc     180 accaacctgt acctgtgcag cctggcctgc tccgacctgc tcatcttcct gtgcatgccg     240
ctcgacctgg tgcgcctgtg gcagtaccgg ccctggacct tcggcgacct gctctgcaaa     300
```

```
ctcttccagt tcgtgagcga gggctgcacc tacgccacgg tgctcaccat acggcgctg      360 agcgtcgagc gctacttcgc catctgcttc ccgctgcgcg ccaaggtgct ggtgaccaag     420
ggccgcgtga agctggccct gctggccatc tgggccgtgg ccttctgcag cgccgggccc     480
atcttcgtgc tggtgggcgt ggagcacgag aacggcaccg accccgggga cacccgcgag     540
tgccgcgcca ccgagttcgc cgtgcgctcg ggctgctca cggccatggt gtgggtgtcc      600
agcgtcttct tcttcctgcc cgtcttctgc ctcacggtgc tctacggcct catcggcagg     660
aagctgtggc ggcgggggcg cggcgacacn gcggggggcg cctcgctccg cgagcagagc     720
caccggcaga cggtgaagat gctcgctgtc gtggtgtttg ctttcatctt ctgctggctg     780
cccttccacg tggggcgata tttattttcc aagtccttcg agcccggctc cttggagatt     840
gctcagatca gccaatactg caacctggta tcctttgtcc tcttctacct cagtgctgcc     900
atcaatccca ttctgtacaa catcatgtcc aagaagtacc gggtggcggt gttcaagctt     960
ctgggatttg aaccttctc ccagaggaag ctctccactc tgaaggatga agttctcgg     1020 gcctggacag agtctagtat taatacatga                                     1050

<210> SEQ ID NO 2
<211> LENGTH: 349
<212> TYPE: PRT
<213> ORGANISM: Canis familiaris

<400> SEQUENCE: 2

Met Arg Asn Ala Thr Ala Arg Glu Gly Pro Gly Ser Ala Gly Trp Asp
 1               5                  10                  15

Leu Leu Pro Leu Phe Pro Ala Pro Leu Leu Ala Gly Val Thr Ala Thr
            20                  25                  30

Cys Val Ala Leu Phe Ala Val Gly Val Ala Gly Asn Leu Leu Thr Val
        35                  40                  45

Leu Val Val Arg Arg Phe Arg Glu Leu Arg Thr Thr Thr Asn Leu Tyr
    50                  55                  60

Leu Cys Ser Leu Ala Cys Ser Asp Leu Leu Ile Phe Leu Cys Met Pro
65                  70                  75                  80

Leu Asp Leu Val Arg Leu Trp Gln Tyr Arg Pro Trp Thr Phe Gly Asp
                85                  90                  95

Leu Leu Cys Lys Leu Phe Gln Phe Val Ser Glu Gly Cys Thr Tyr Ala
            100                 105                 110

Thr Val Leu Thr Ile Thr Ala Leu Ser Val Glu Arg Tyr Phe Ala Ile
        115                 120                 125

Cys Phe Pro Leu Arg Ala Lys Val Leu Val Thr Lys Gly Arg Val Lys
    130                 135                 140

Leu Ala Leu Leu Ala Ile Trp Ala Val Ala Phe Cys Ser Ala Gly Pro
145                 150                 155                 160

Ile Phe Val Leu Val Gly Val Glu His Glu Asn Gly Thr Asp Pro Arg
                165                 170                 175

Asp Thr Arg Glu Cys Arg Ala Thr Glu Phe Ala Val Arg Ser Gly Leu
            180                 185                 190

Leu Thr Ala Met Val Trp Val Ser Ser Val Phe Phe Leu Pro Val
        195                 200                 205

Phe Cys Leu Thr Val Leu Tyr Gly Leu Ile Gly Arg Lys Leu Trp Arg
    210                 215                 220

Arg Gly Arg Gly Asp Thr Ala Gly Gly Ala Ser Leu Arg Glu Gln Ser
225                 230                 235                 240
```

```
His Arg Gln Thr Val Lys Met Leu Ala Val Val Phe Ala Phe Ile
            245                 250                 255

Phe Cys Trp Leu Pro Phe His Val Gly Arg Tyr Leu Phe Ser Lys Ser
        260                 265                 270

Phe Glu Pro Gly Ser Leu Glu Ile Ala Gln Ile Ser Gln Tyr Cys Asn
            275                 280                 285

Leu Val Ser Phe Val Leu Phe Tyr Leu Ser Ala Ala Ile Asn Pro Ile
        290                 295                 300

Leu Tyr Asn Ile Met Ser Lys Lys Tyr Arg Val Ala Val Phe Lys Leu
305                 310                 315                 320

Leu Gly Phe Glu Pro Phe Ser Gln Arg Lys Leu Ser Thr Leu Lys Asp
                325                 330                 335

Glu Ser Ser Arg Ala Trp Thr Glu Ser Ser Ile Asn Thr
                340                 345

<210> SEQ ID NO 3
<211> LENGTH: 18
<212> TYPE: DNA
<213> ORGANISM: Canis familiaris

<400> SEQUENCE: 3
atgcggaacg cgacggcc                                                       18

<210> SEQ ID NO 4
<211> LENGTH: 18
<212> TYPE: DNA
<213> ORGANISM: Canis familiaris

<400> SEQUENCE: 4
tcatgtatta atacttag                                                       18

<210> SEQ ID NO 5
<211> LENGTH: 366
<212> TYPE: PRT
<213> ORGANISM: Homo sapiens

<400> SEQUENCE: 5

Met Trp Asn Ala Thr Pro Ser Glu Glu Pro Gly Phe Asn Leu Thr Leu
1               5                   10                  15

Ala Asp Leu Asp Trp Asp Ala Ser Pro Gly Asn Asp Ser Leu Gly Asp
            20                  25                  30

Glu Leu Leu Gln Leu Phe Pro Ala Pro Leu Leu Ala Gly Val Thr Ala
        35                  40                  45

Thr Cys Val Ala Leu Phe Val Val Gly Ile Ala Gly Asn Leu Leu Thr
    50                  55                  60

Met Leu Val Val Ser Arg Phe Arg Glu Leu Arg Thr Thr Thr Asn Leu
65                  70                  75                  80

Tyr Leu Ser Ser Met Ala Phe Ser Asp Leu Leu Ile Phe Leu Cys Met
                85                  90                  95

Pro Leu Asp Leu Val Arg Leu Trp Gln Tyr Arg Pro Trp Asn Phe Gly
            100                 105                 110

Asp Leu Leu Cys Lys Leu Phe Gln Phe Val Ser Glu Ser Cys Thr Tyr
        115                 120                 125

Ala Thr Val Leu Thr Ile Thr Ala Leu Ser Val Glu Arg Tyr Phe Ala
    130                 135                 140

Ile Cys Phe Pro Leu Arg Ala Lys Val Val Thr Lys Gly Arg Val
145                 150                 155                 160
```

-continued

Lys Leu Val Ile Phe Val Ile Trp Ala Val Ala Phe Cys Ser Ala Gly
            165                 170                 175

Pro Ile Phe Val Leu Val Gly Val Glu His Glu Asn Gly Thr Asp Pro
            180                 185                 190

Trp Asp Thr Asn Glu Cys Arg Pro Thr Glu Phe Ala Val Arg Ser Gly
            195                 200                 205

Leu Leu Thr Val Met Val Trp Val Ser Ser Ile Phe Phe Leu Pro
    210                 215                 220

Val Phe Cys Leu Thr Val Leu Tyr Ser Leu Ile Gly Arg Lys Leu Trp
225                 230                 235                 240

Arg Arg Arg Arg Gly Asp Ala Val Val Gly Ala Ser Leu Arg Asp Gln
                245                 250                 255

Asn His Lys Gln Thr Val Lys Met Leu Ala Val Val Phe Ala Phe
            260                 265                 270

Ile Leu Cys Trp Leu Pro Phe His Val Gly Arg Tyr Leu Phe Ser Lys
            275                 280                 285

Ser Phe Glu Pro Gly Ser Leu Glu Ile Ala Gln Ile Ser Gln Tyr Cys
    290                 295                 300

Asn Leu Val Ser Phe Val Leu Phe Tyr Leu Ser Ala Ala Ile Asn Pro
305                 310                 315                 320

Ile Leu Tyr Asn Ile Met Ser Lys Lys Tyr Arg Val Ala Val Phe Arg
            325                 330                 335

Leu Leu Gly Phe Glu Pro Phe Ser Gln Arg Lys Leu Ser Thr Leu Lys
            340                 345                 350

Asp Glu Ser Ser Arg Ala Trp Thr Glu Ser Ser Ile Asn Thr
            355                 360                 365

<210> SEQ ID NO 6
<211> LENGTH: 364
<212> TYPE: PRT
<213> ORGANISM: Rattus norvegicus

<400> SEQUENCE: 6

Met Trp Asn Ala Thr Pro Ser Glu Glu Pro Glu Pro Asn Val Thr Leu
1               5                   10                  15

Asp Leu Asp Trp Asp Ala Ser Pro Gly Asn Asp Ser Leu Pro Asp Glu
            20                  25                  30

Leu Leu Pro Leu Phe Pro Ala Pro Leu Leu Ala Gly Val Thr Ala Thr
        35                  40                  45

Cys Val Ala Leu Phe Val Val Gly Ile Ser Gly Asn Leu Leu Thr Met
    50                  55                  60

Leu Val Val Ser Arg Phe Arg Glu Leu Arg Thr Thr Thr Asn Leu Tyr
65                  70                  75                  80

Leu Ser Ser Met Ala Phe Ser Asp Leu Leu Ile Phe Leu Cys Met Pro
            85                  90                  95

Leu Asp Leu Val Arg Leu Trp Gln Tyr Arg Pro Trp Asn Phe Gly Asp
            100                 105                 110

Leu Leu Cys Lys Leu Phe Gln Phe Val Ser Glu Ser Cys Thr Tyr Ala
        115                 120                 125

Thr Val Leu Thr Ile Thr Ala Leu Ser Val Glu Arg Tyr Phe Ala Ile
    130                 135                 140

Cys Phe Pro Leu Arg Ala Lys Val Val Thr Lys Gly Arg Val Lys
145                 150                 155                 160

Leu Val Ile Leu Val Ile Trp Ala Val Ala Phe Cys Ser Ala Gly Pro
            165                 170                 175

-continued

```
Ile Phe Val Leu Val Gly Val Glu His Glu Asn Gly Thr Asp Pro Arg
            180                 185                 190

Asp Thr Asn Glu Cys Arg Ala Thr Glu Phe Ala Val Arg Ser Gly Leu
        195                 200                 205

Leu Thr Val Met Val Trp Val Ser Val Phe Phe Leu Pro Val
        210                 215                 220

Phe Cys Leu Thr Val Leu Tyr Ser Leu Ile Gly Arg Lys Leu Trp Arg
225                 230                 235                 240

Arg Arg Gly Asp Ala Ala Val Gly Ala Ser Leu Arg Asp Gln Asn His
                245                 250                 255

Lys Gln Thr Val Lys Met Leu Ala Val Val Phe Ala Phe Ile Leu
        260                 265                 270

Cys Trp Leu Pro Phe His Val Gly Arg Tyr Leu Phe Ser Lys Ser Phe
        275                 280                 285

Glu Pro Gly Ser Leu Glu Ile Ala Gln Ile Ser Gln Tyr Cys Asn Leu
        290                 295                 300

Val Ser Phe Val Leu Phe Tyr Leu Ser Ala Ala Ile Asn Pro Ile Leu
305                 310                 315                 320

Tyr Asn Ile Met Ser Lys Lys Tyr Arg Val Ala Val Phe Lys Leu Leu
                325                 330                 335

Gly Phe Glu Ser Phe Ser Gln Arg Lys Leu Ser Thr Leu Lys Asp Glu
        340                 345                 350

Ser Ser Arg Ala Trp Thr Lys Ser Ser Ile Asn Thr
        355                 360
```

<210> SEQ ID NO 7
<211> LENGTH: 366
<212> TYPE: PRT
<213> ORGANISM: Sus scrofa

<400> SEQUENCE: 7

```
Met Trp Asn Ala Thr Pro Ser Glu Glu Pro Gly Pro Asn Leu Thr Leu
1               5                   10                  15

Pro Asp Leu Gly Trp Asp Ala Pro Pro Glu Asn Asp Ser Leu Val Glu
            20                  25                  30

Glu Leu Leu Pro Leu Phe Pro Thr Pro Leu Leu Ala Gly Val Thr Ala
        35                  40                  45

Thr Cys Val Ala Leu Phe Val Val Gly Ile Ala Gly Asn Leu Leu Thr
    50                  55                  60

Met Leu Val Val Ser Arg Phe Arg Glu Met Arg Thr Thr Thr Asn Leu
65                  70                  75                  80

Tyr Leu Ser Ser Met Ala Phe Ser Asp Leu Leu Ile Phe Leu Cys Met
                85                  90                  95

Pro Leu Asp Leu Phe Arg Leu Trp Gln Tyr Arg Pro Trp Asn Leu Gly
            100                 105                 110

Asn Leu Leu Cys Lys Leu Phe Gln Phe Val Ser Glu Ser Cys Thr Tyr
        115                 120                 125

Ala Thr Val Leu Thr Ile Thr Ala Leu Ser Val Glu Arg Tyr Phe Ala
    130                 135                 140

Ile Cys Phe Pro Leu Arg Ala Lys Val Val Thr Lys Gly Arg Val
145                 150                 155                 160

Lys Leu Val Ile Leu Val Ile Trp Ala Val Ala Phe Cys Ser Ala Gly
                165                 170                 175

Pro Ile Phe Val Leu Val Gly Val Glu His Asp Asn Gly Thr Asp Pro
```

```
                    180                 185                 190
Arg Asp Thr Asn Glu Cys Arg Ala Thr Glu Phe Ala Val Arg Ser Gly
            195                 200                 205

Leu Leu Thr Val Met Val Trp Val Ser Ser Val Phe Phe Phe Leu Pro
        210                 215                 220

Val Phe Cys Leu Thr Val Leu Tyr Ser Leu Ile Gly Arg Lys Leu Trp
225                 230                 235                 240

Arg Arg Lys Arg Gly Glu Ala Ala Val Gly Ser Ser Leu Arg Asp Gln
                245                 250                 255

Asn His Lys Gln Thr Val Lys Met Leu Ala Val Val Val Phe Ala Phe
                260                 265                 270

Ile Leu Cys Trp Leu Pro Phe His Val Gly Arg Tyr Leu Phe Ser Lys
            275                 280                 285

Ser Leu Glu Pro Gly Ser Val Glu Ile Ala Gln Ile Ser Gln Tyr Cys
        290                 295                 300

Asn Leu Val Ser Phe Val Leu Phe Tyr Leu Ser Ala Ala Ile Asn Pro
305                 310                 315                 320

Ile Leu Tyr Asn Ile Met Ser Lys Lys Tyr Arg Val Ala Val Phe Lys
                325                 330                 335

Leu Leu Gly Phe Glu Pro Phe Ser Gln Arg Lys Leu Ser Thr Leu Lys
            340                 345                 350

Asp Glu Ser Ser Arg Ala Trp Thr Glu Ser Ser Ile Asn Thr
            355                 360                 365

<210> SEQ ID NO 8
<211> LENGTH: 39
<212> TYPE: DNA
<213> ORGANISM: Canis familiaris

<400> SEQUENCE: 8
gggcccgaat tcgccgccat gcggaacgcg acggcccgc                            39

<210> SEQ ID NO 9
<211> LENGTH: 38
<212> TYPE: DNA
<213> ORGANISM: Canis familiaris

<400> SEQUENCE: 9
agtttagcgg ccgctcatgt attaatacta gactctgt                             38
```